Figure 1:
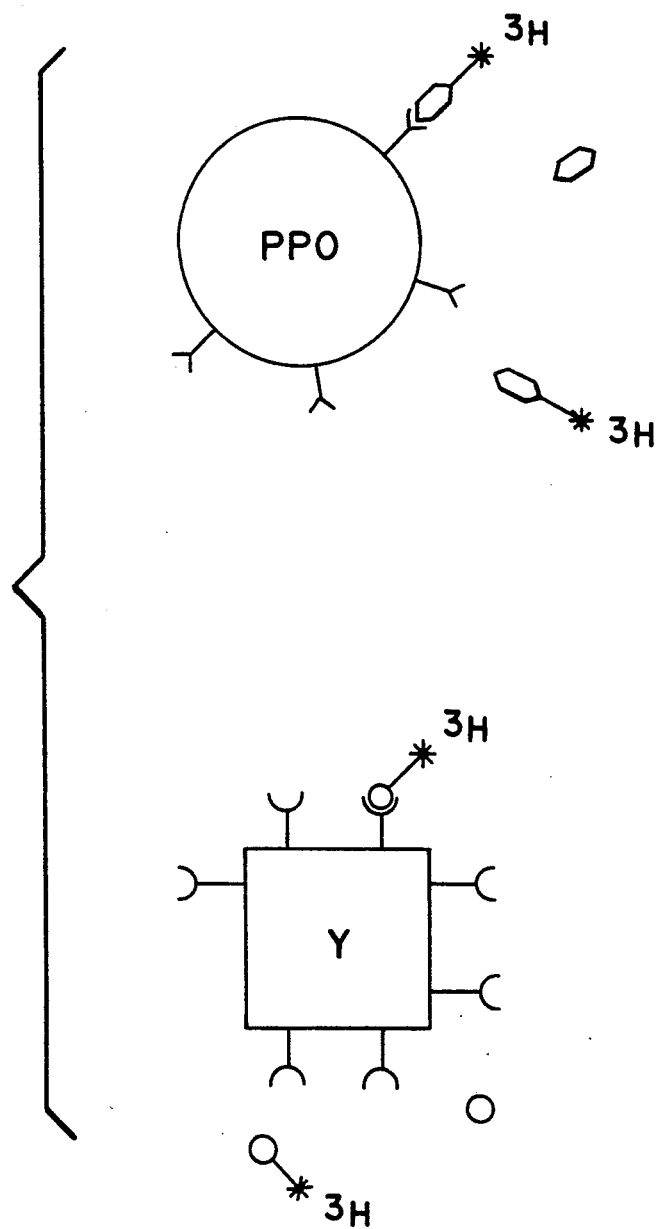

United States Patent [19]

Potter et al.

[11] Patent Number: 5,246,869

[45] Date of Patent: Sep. 21, 1993

[54] METHOD FOR THE SIMULTANEOUS ASSAY OF LIGANDS

[75] Inventors: Colin Potter; Gerald Warner, both of Headington, England; Timo Oikari, Turku, Finland

[73] Assignee: Wallac Oy, Turku, Finland

[21] Appl. No.: 761,836

[22] PCT Filed: Mar. 21, 1990

[86] PCT No.: PCT/FI90/00073

§ 371 Date: Sep. 23, 1991

§ 102(e) Date: Sep. 23, 1991

[87] PCT Pub. No.: WO90/11524

PCT Pub. Date: Oct. 4, 1990

[30] Foreign Application Priority Data

Mar. 22, 1989 [FI] Finland .................................. 891354

[51] Int. Cl.[5] .......................................... G01N 33/543
[52] U.S. Cl. .................................... 436/518; 436/524; 436/528; 436/534; 436/804; 252/301.17
[58] Field of Search .................. 252/301.17; 435/973, 435/7.1; 436/518, 524, 528, 527, 804, 534

[56] References Cited

U.S. PATENT DOCUMENTS 4,016,250 4/1977 Saxena .......................... 436/804 X
4,568,649 2/1986 Bertoglio et al. .................. 436/534

OTHER PUBLICATIONS

George T. Reynolds, "Solid and Liquid Scintillation Counters", *Nucleonics,* vol. 10, No. 7, pp. 46-53, (1952).
"Latest Developments in Scintillation Counting", *Nucleonics,* vol. 10, No. 3, pp. 32-41, (1952).
Bosworth et al., "Scintillation Proximity Assay," *Nature,* vol. 341, pp. 167-168, (1989).

*Primary Examiner*—Esther L. Kepplinger
*Assistant Examiner*—Susan C. Wolski
*Attorney, Agent, or Firm*—Shea & Gould

[57] ABSTRACT

The objective of the present invention is a method for determining two or more radioactively labeled ligands simultaneously in the same sample. According to the invention the ligands are determined with proximity assay so that for determining said ligands support materials with different scintillation characteristics are employed, each said support material having attached onto it molecules specifically binding one of said ligands. The support material consists totally or partially of scintillator.

6 Claims, 1 Drawing Sheet

METHOD FOR THE SIMULTANEOUS ASSAY OF LIGANDS

The invention relates to a method for the simultaneous assay of two or more radioactively labeled ligands.

The U.S. Pat. No. 4,568,649 describes a proximity assay for ligands whereby biomolecules capable of specifically binding the ligands are attached or coated onto scintillating support medium. Such biomolecules are e.g. immunoglobulins, receptors or nucleic acids. The support medium can be e.g. in the form of small beads.

According to the assay, the solution containing a known amount of radioactively labeled ligand and an unknown amount of unlabeled, but otherwise similar investigated ligand, is incubated with the beads. Alternatively, an amount of radioactively labeled ligand can be incubated with the beads. If the isotope used as the label is low-energetic, e.g. tritium, the emitted electrons or beta-particles have ranges less than a few micrometers and only the label that gets bound and thus gets in close proximity to the scintillating material produces bursts of light called scintillations. These can be detected with a liquid scintillation counter. The unbound label remains too far to produce scintillations. The competition between labeled and unlabeled ligands results in that the more there is investigated, i.e. unlabeled, ligand present in the solution, the less of the labeled ligand will get bound and the less scintillations are produced.

A great advantage of the described assay is that it does not require separation of the unbound and bound label fractions. A disadvantage is that while being suspended in the solution the beads can settle down affecting adversely in binding and output of scintillation light. Dispensing the beads, e.g. by pipetting, can also be problematic.

As an improvement a support structure has been proposed in which scintillating compounds called scintillators are processed in or onto fibers forming a filter mat. The mat also retains liquid by capillary forces.

Although no separation steps are necessary in proximity assays, the samples still require dispensing into different sample containers in different ligand assays. If several ligands are to be assayed from the same sample, the total sample volume may limit the number of assays that can be performed. In a busy laboratory the manipulation of many sample containers and the availability of counting facilities may limit throughput. Although usage of other isotopes, such as $^{14}C$ and $^{35}S$, as extra labels could be possible in principle, beta-particle ranges of their emissions are long and can produce scintillations even without the label being bound. A consequence would be increase in the background count rate.

The objective of the present invention is to develop a method that does not have the drawbacks mentioned above. The method described by the invention is characterized in that ligands are assayed simultaneously in the same sample by using proximity assay so that for determining the ligands support materials with different scintillation characteristics are employed, each said support material having attached onto it molecules specifically binding one of said ligands.

According to one advantageous embodiment the support material consists totally or partially of scintillator.

With the invention several ligands can be assayed simultaneously. Furthermore, a great advantage is that each ligand can be labeled with the same low-energetic isotope, such as tritium. The contributions of each ligand to the measured scintillation count rate can be determined if each binding molecule type is attached onto different scintillating support material, which differ in some measurable characteristic of the scintillation light. The support material can be in the form of e.g. beads or fibers.

One scintillation characteristic that can be utilized in the present invention is the different light output of different scintillators upon excitation by electrons of the same energy. This manifests as a characteristic pulse height distribution or spectrum when counted in a liquid scintillation counter. Consequently, according to another advantageous embodiment in support materials scintillators are used that differ in their scintillation pulse height. The composite spectrum produced by the investigated sample can then be analyzed by using some known spectrum analysis technique, e.g. channels ratio counting or least squares fitting. These handle proportions of spectra in appropriate regions, such as windows or channels.

In the mentioned spectrum analysis techniques the region information of each individual scintillator has been stored beforehand in the counter memory with suitable standard samples. Thus the contribution of each scintillator to the composite spectrum can be determined. The mentioned spectrum analysis techniques have earlier been employed in liquid scintillation multilabel counting where there are several different isotopes dissolved in the same liquid scintillator and the amounts of the isotopes are to be determined. Different isotopes have different decay energies and thus different spectra.

Contrary to multilabel counting the present invention relates to a situation where only one isotope but several types of scintillators are employed e.g. in the form of beads so that each bead type binds only ligand specific to it and produces a spectrum typical to that particular scintillator. Examples of scintillators producing a low spectrum are plastic scintillators, diphenyloxazole or PPO and butyl-PBD. A higher spectrum is obtained from anthracene and from some inorganic scintillators, such as cerium-activated yttrium silicate $Y_2SiO_5$ (Ce).

Another characteristic differing between different scintillators and that can be utilized in the invention is the temporal length or shape of the scintillation pulses. For instance, the pulse length of plastic scintillators is less than ten nanoseconds whereas that of yttrium silicate is over one hundred nanoseconds. There exist electronic pulse shape analyzers and discriminators that produce a signal proportional to pulse length. This property can be employed with same techniques as the above described pulse height distributions. Consequently, according to a third advantageous embodiment, in support materials scintillators are used that differ in their scintillation pulse shape.

From the above it is evident that at least two different scintillators can be resolved with the scintillation characteristics like pulse height and shape. Considerable savings are then achieved in working time, number of samples and counting time.

The invention is clarified by the following example with reference to the enclosed drawing that shows schematically two different scintillator beads and two different ligands labeled by the same isotope. In the figure there are shown diphenyloxazole or PPO and cerium-activated yttriumsilicate or $Y_2SiO_5$ (Ce), abbreviated by the letter Y, in the form of beads. Both scintillators bind only ligands specific to them. Ligands are labeled by the same radioactive isotope which is low-energetic tritium or $^3$H. The labeled ligand molecules compete with the unlabeled or investigated ligand molecules for binding to the catching molecules attached onto scintillators. In the employed proximity assay only the bound labeled ligand is in close enough proximity to cause a scintillation. With a scintillation counter the amount of investigated sample can be determined.

It is evident for those skilled in the art that the different embodiments of the invention can vary within the scope presented by the claims below.

We claim:

1. A proximity assay method for simultaneously assaying two or more different and radioactively labeled ligands, comprising:

incubating in a single assay container a sample containing two or more different and radioactively labeled ligands with two or more scintillative support materials, wherein said radioactively labeled ligands are labeled with a low energy isotope and each of said two or more scintillative support materials have different scintillation characteristics and each of said two or more scintillative support materials have attached to it biomolecules which specifically bind one of said two or more ligands, such than any of said two or more different and radioactively labeled ligands present in said sample will bind to each of said two or more scintillative support materials, and wherein the scintillative support materials are in close enough proximity to any bound radioactively labeled ligands to produce scintillations and are too far from any unbound radioactively labeled ligands to produce scintillations;

measuring the scintillation light output contribution produced by each of said two or more scintillative support materials; and based on said scintillation light output contributions, determining the amount of each of the two or more different ligands in the sample.

2. A method according to claim 1, wherein the two or more scintillative support materials differ in scintillation pulse height.

3. A method according to claim 1, wherein the two or more scintillative support materials differ in scintillation pulse shape.

4. A method according to claim 1, wherein the two or more scintillative support materials differ in two or more scintillation characteristics.

5. A method according to claim 1, wherein the two or more radioactively labeled ligands are labeled with the said radioisotope.

6. A method according to claim 5, wherein the radioisotope is H-3.

* * * * *